(12) United States Patent
Nakata et al.

(10) Patent No.: US 8,294,113 B2
(45) Date of Patent: Oct. 23, 2012

(54) IMAGE DETECTING DEVICE AND IMAGE CAPTURING SYSTEM

(75) Inventors: Hajime Nakata, Minami-ashigara (JP); Kuniaki Miyako, Minami-ashigara (JP); Kazuo Hakamata, Odawara (JP); Yasunori Ohta, Yokohama (JP)

(73) Assignee: FUJIFILM Corporation, Tokyo (JP)

( * ) Notice: Subject to any disclaimer, the term of this patent is extended or adjusted under 35 U.S.C. 154(b) by 972 days.

(21) Appl. No.: 12/335,614

(22) Filed: Dec. 16, 2008

(65) Prior Publication Data

US 2009/0101828 A1  Apr. 23, 2009

Related U.S. Application Data

(63) Continuation-in-part of application No. 12/239,799, filed on Sep. 28, 2008, now abandoned.

(30) Foreign Application Priority Data

Sep. 28, 2007  (JP) .................. 2007-253427
Sep. 26, 2008  (JP) .................. 2008-247039

(51) Int. Cl.
  *G01T 1/24*  (2006.01)
(52) U.S. Cl. .................................. 250/370.15
(58) Field of Classification Search ......... 250/370.01–370.15; 378/98.8
See application file for complete search history.

(56) References Cited

U.S. PATENT DOCUMENTS

| | | | |
|---|---|---|---|
| 6,323,891 B1 | 11/2001 | Kitani et al. | |
| 6,333,963 B1 * | 12/2001 | Kaifu et al. | 378/98.2 |
| 6,469,312 B2 | 10/2002 | Agano | |
| 7,006,599 B2 * | 2/2006 | Okamura et al. | 378/98.11 |
| 7,010,091 B2 | 3/2006 | Hayashida et al. | |
| 7,016,466 B2 * | 3/2006 | Rinaldi et al. | 378/98.8 |
| 7,078,703 B2 | 7/2006 | Watanabe | |
| 2004/0086204 A1 | 5/2004 | Shoji | |

FOREIGN PATENT DOCUMENTS

| | | |
|---|---|---|
| JP | 61-144487 U | 9/1986 |
| JP | 10-256613 A | 9/1998 |
| JP | 11-271456 A | 10/1999 |
| JP | 11-345956 A | 12/1999 |
| JP | 2001-281345 A | 10/2001 |
| JP | 2002-250772 A | 9/2002 |
| JP | 2003-014860 A | 1/2003 |
| JP | 2004-049887 A | 2/2004 |
| JP | 2004-144713 A | 5/2004 |
| JP | 2005-009674 A | 4/2005 |
| JP | 2006-247102 A | 9/2006 |
| JP | 2007-185375 A | 7/2007 |

OTHER PUBLICATIONS

Rejection of the Application, dated Apr. 24, 2012, issued in related JP Application No. 2008-247039, 6 pages in English and Japanese.

* cited by examiner

Primary Examiner — Kiho Kim
(74) Attorney, Agent, or Firm — Sughrue Mion, PLLC

(57) ABSTRACT

An image detecting device includes an image detector, a temperature regulation controller, an image information output detector, and a timer, wherein the temperature regulation controller stops or relaxes the temperature regulation control operation on the image detector based on the image information output detection signal input thereto from the image information output detector, and resumes or stops relaxing the temperature regulation control operation on the image detector when the timer has measured a preset period of time after the temperature regulation control operation has been stopped or relaxed.

21 Claims, 9 Drawing Sheets

IMAGE DETECTING DEVICE AND IMAGE CAPTURING SYSTEM

This is a Continuation-In-Part of application Ser. No. 12/239,799 filed Sep. 28, 2008. The entire disclosure of the prior application, application number U.S. Ser. No. 12/239,799, is hereby incorporated by reference.

BACKGROUND OF THE INVENTION

1. Field of the Invention

The present invention relates to an image detecting device for outputting image information representative of an image recorded in a given recording area, and to an image capturing system that incorporates such an image detecting device therein.

2. Description of the Related Art

In the medical field, there have widely been used image capturing apparatuses, which apply radiation from a radiation source to a subject (a patient) and detect the radiation that has passed through the subject with an image detector, in order to acquire radiation image information of the subject.

Japanese Laid-Open Patent Publication No. 2003-014860 discloses that the temperature of a radiation detector, such as a CCD or the like, is detected by a temperature sensor and controlled to reach a predetermined temperature by way of temperature regulation, for preventing the radiation detector from suffering from dew condensation.

When an image detector such as a radiation detector or the like operates to read a detected image, i.e., to output detected image information, if a temperature regulating means, such as a cooling fan or the like, is energized to regulate the temperature of the image detector, the drive signal that energizes the temperature regulating means may potentially be added to the image information, thus degrading the quality of the read image.

If the image detector is continuously kept at a certain temperature under temperature regulation control in order to achieve a desired performance of the image detector, then energy is wastefully consumed for carrying out the temperature regulation control process. Japanese Laid-Open Patent Publication No. 2003-014860 discloses nothing concerning specific details of temperature regulation upon reading a detected image from the radiation detector.

SUMMARY OF THE INVENTION

It is an object of the present invention to provide an image detecting device and an image capturing system, which avoid unnecessary temperature regulation control so as to save energy, and which are capable of obtaining high-quality images.

An image detecting device according to the present invention comprises an image detector for recording an image therein and outputting the recorded image as image information, a temperature regulation controller for performing a temperature regulation control operation in order to adjust the image detector to a predetermined temperature, an image information output detector for detecting the output of image information from the image detector and outputting the detected output as an image information output detection signal to the temperature regulation controller, and a timer. The temperature regulation controller stops or relaxes a temperature regulation control operation on the image detector based on the image information output detection signal input thereto, and resumes or stops relaxing the temperature regulation control operation on the image detector when the timer has measured a preset period of time after having stopped or relaxed the temperature regulation control operation.

When an image is read, i.e., when image information is output, the temperature regulation controller stops or relaxes the temperature regulation control operation on the image detector. When the timer has measured the preset period of time after the temperature regulation control operation has been stopped or relaxed, the temperature regulation controller resumes the normal temperature regulation control operation on the image detector. As a result, noise caused by the temperature regulation control operation is prevented from being added to the image, i.e., to the image information, and hence the image that is produced is high in quality.

Furthermore, the normal temperature regulation control operation is resumed upon elapse of the preset period of time after the temperature regulation control operation has been temporarily shut off or relaxed. Therefore, the temperature regulation control operation is appropriately performed only during time periods other than when the image is read. Accordingly, the radiation detector remains stably operational. As a result, unnecessary temperature regulation control is avoided in order to save energy consumed by the radiation detecting device, and by the overall image capturing system that incorporates the radiation detecting device therein.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
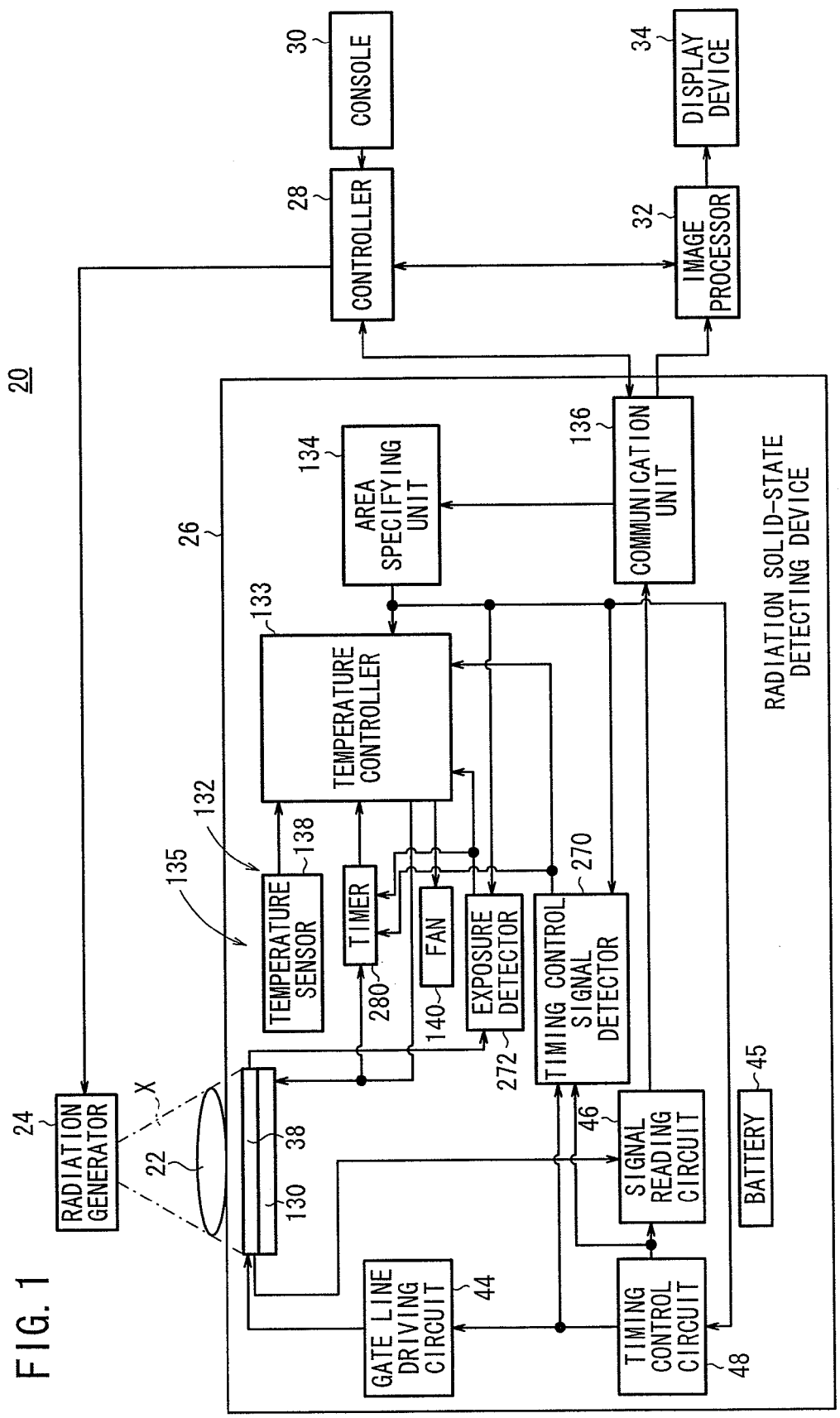
FIG. 1 is a block diagram of an image capturing system according to an embodiment of the present invention.

As shown in FIG. 1, an image capturing system 20 according to an embodiment of the present invention comprises a radiation generator 24 for generating and applying radiation X to a subject 22, typically a patient, a radiation solid-state detecting device (an image detecting device, a radiation image information detecting device) 26 for detecting radiation X that has passed through the subject 22, a controller 28 for controlling the radiation generator 24 and the radiation solid-state detecting device 26, a console 30 for setting image capturing conditions such as a radiation dose for the radiation X to be applied to the subject 22 in the controller 28, an image processor 32 for processing radiation image information of the subject 22, which is read from the radiation solid-state detecting device 26, and a display device 34 for displaying the processed radiation image information.

The radiation solid-state detecting device 26 comprises a sensor substrate (image detector) 38, a gate line driving circuit 44, a battery 45, a signal reading circuit 46, a timing control circuit 48, a temperature regulation controller 135, an area specifying unit 134, a communication unit 136, a timing control signal detector (image information output detector) 270, an exposure detector (image recording detector) 272, and a timer (time measuring unit) 280. The temperature regulation controller 135 comprises a cooling panel 130 and a cooling panel energizing unit 132. The cooling panel energizing unit 132 comprises a temperature controller 133, a temperature sensor 138, and a fan (a cooling fan) 140.

Figure 2:
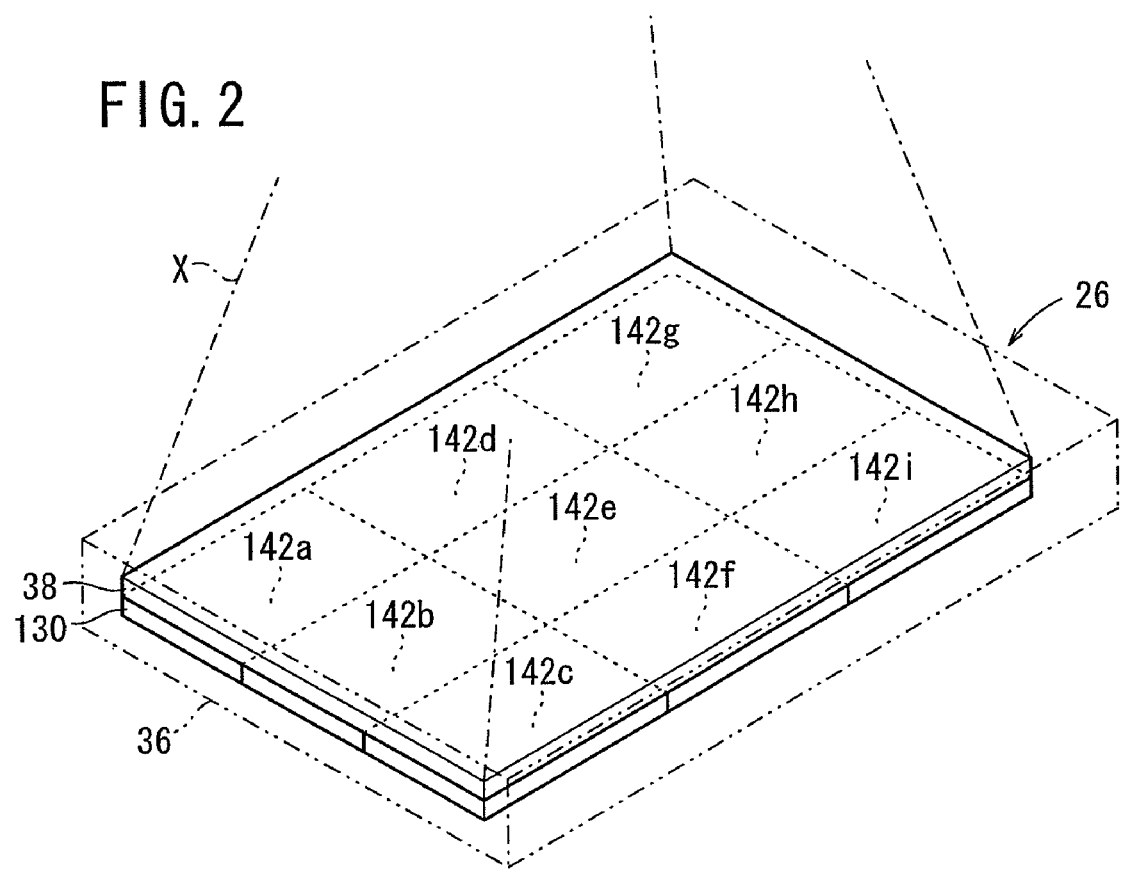
FIG. 2 is a perspective view of the radiation solid-state detecting device shown in FIG. 1, with a cooling panel disposed on the rear surface of a sensor substrate.

FIG. 2 shows the radiation solid-state detecting device 26 in perspective. As shown in FIG. 2, the radiation solid-state detecting device 26 comprises a sensor substrate 38 housed in a protective casing 36 for storing (recording) radiation image information carried by radiation X that has passed through the subject 22 (see FIG. 1) as two-dimensional electric charge information, and a cooling panel 130 held closely against a rear surface of the sensor substrate 38, which is opposite to a front surface thereof that is irradiated with radiation X.

The cooling panel 130 is disposed substantially fully over the rear surface of the sensor substrate 38, and comprises nine rectangular cooling units 142a through 142i placed on the rear surface of the sensor substrate 38.

Figure 3:
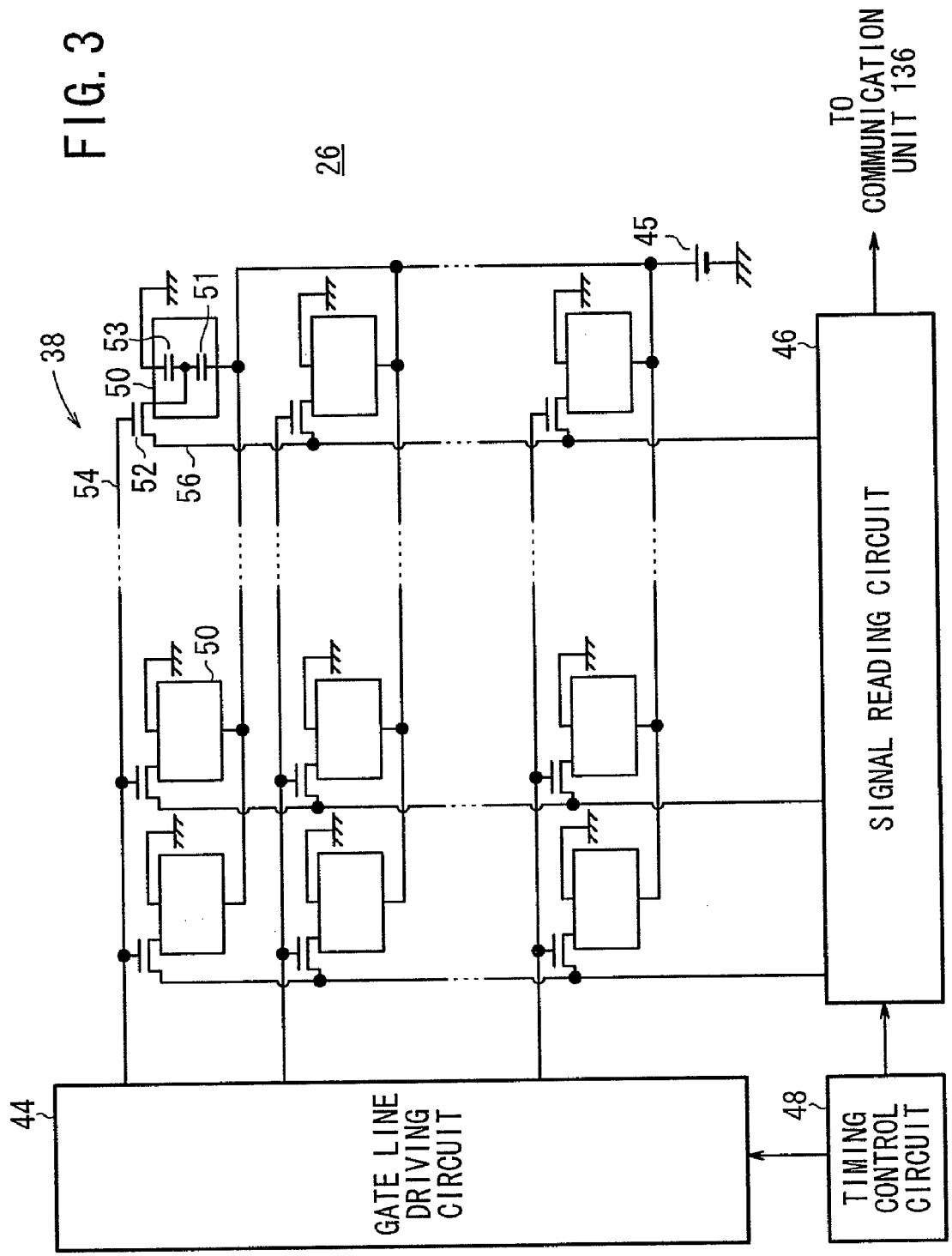
FIG. 3 is a block diagram of the radiation solid-state detecting device shown in FIG. 1.

FIG. 3 shows the radiation solid-state detecting device 26 in block form. As shown in FIG. 3, the radiation solid-state detecting device 26 comprises the sensor substrate 38, a gate line driving circuit 44 having a plurality of driving ICs, not shown, a signal reading circuit 46 having a plurality of reading ICs 42 (see FIG. 4), and a timing control circuit 48 for controlling the gate line driving circuit 44 and the signal reading circuit 46.

The sensor substrate 38 comprises an array of thin-film transistors (TFTs) 52 arranged in rows and columns, a photoelectric conversion layer 51 made of a material such as amorphous selenium (a-Se) for generating electric charges upon detection of radiation X, the photoelectric conversion layer 51 being disposed on the array of TFTs 52, and an array of storage capacitors 53 connected to the photoelectric conversion layer 51. When radiation X is applied to the sensor substrate 38, the photoelectric conversion layer 51 generates electric charges, and the storage capacitors 53 store the generated electric charges therein. Then, the TFTs 52 are turned on, each row at a time, in order to read the electric charges from the storage capacitors 53 as an image signal. In FIG. 3, the photoelectric conversion layer 51 and one of the storage capacitors 53 are shown as making up a pixel 50, wherein the pixel 50 is connected to one of the TFTs 52. Details of the other pixels 50 are omitted from illustration. Since amorphous selenium tends to change in structure and lose functions thereof at high temperatures, amorphous selenium needs to be used within a certain temperature range. Therefore, some means for cooling the sensor substrate 38 should preferably be provided in the radiation solid-state detecting device 26. The TFTs 52 connected to the respective pixels 50 are connected to respective gate lines 54 extending parallel to the rows, and to respective signal lines 56 extending parallel to the columns. The gate lines 54 are connected to the gate line driving circuit 44, and the signal lines 56 are connected to the signal reading circuit 46.

Figure 4:
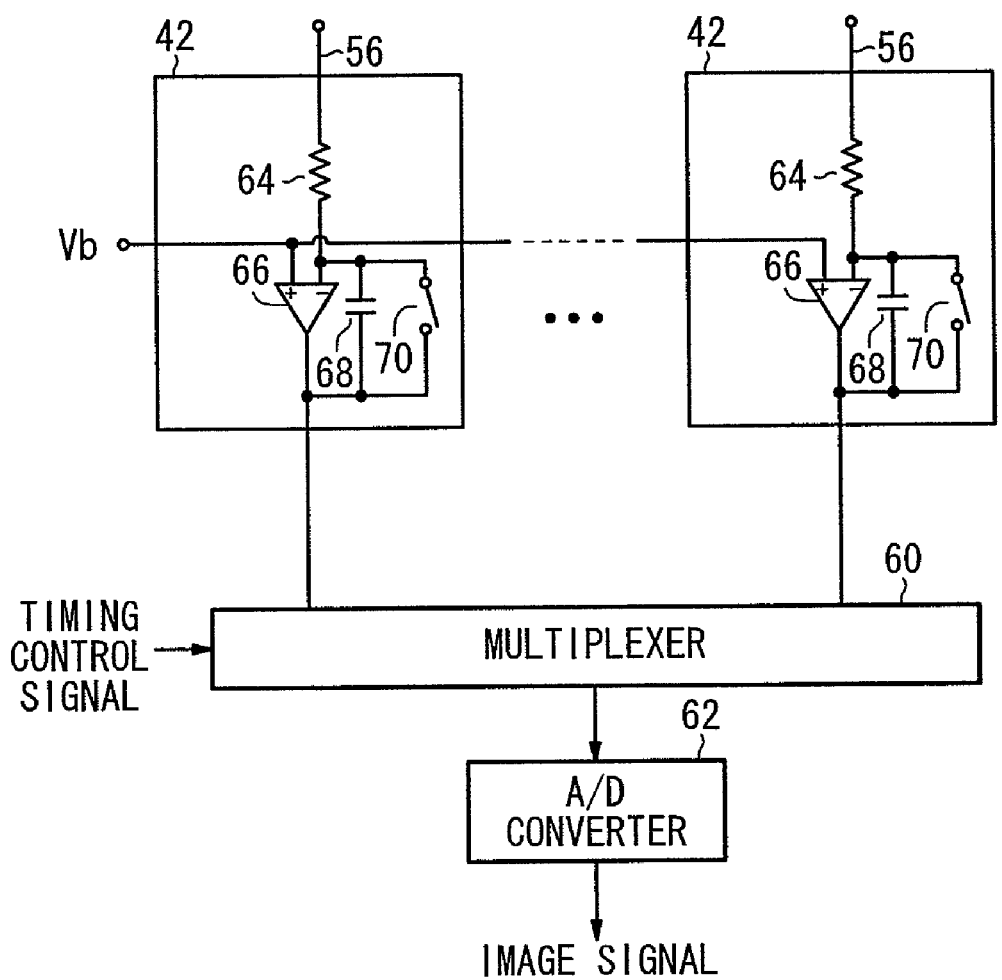
FIG. 4 is a detailed block diagram of a signal reading circuit shown in FIG. 3.

FIG. 4 shows the signal reading circuit 46 in detailed block form. As shown in FIG. 4, the signal reading circuit 46 comprises a plurality of reading ICs 42 connected to the respective signal lines 56 of the sensor substrate 38 (see FIGS. 1 through 3), a multiplexer 60 for selecting pixels 50 connected to one of the signal lines 56 based on timing signals from the timing control circuit 48, and an A/D converter 62 for converting radiation image information read from the selected pixels into digital image signals and sending (outputting) the digital image signals via the communication unit 136 to the image processor 32.

Each of the reading ICs 42 comprises an operational amplifier (integrating amplifier) 66 for detecting current supplied from the signal line 56 through a resistor 64, an integrating capacitor 68, and a switch 70. The operational amplifier 66 has an inverting input terminal connected to the signal line 56 through the resistor 64, and a non-inverting input terminal supplied with a reference voltage Vb.

Figure 5:
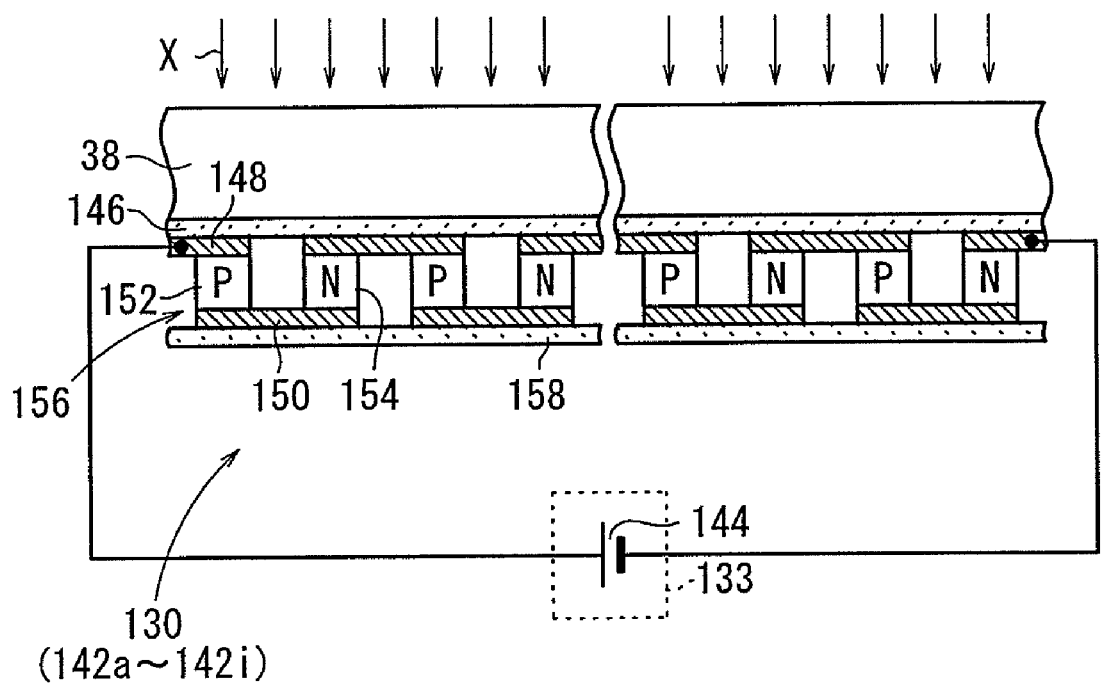
FIG. 5 is a fragmentary cross-sectional view of the sensor substrate and the cooling panel shown in FIG. 2.

FIG. 5 shows in fragmentary cross section the sensor substrate 38 and the cooling panel 130 (see FIGS. 1 and 2).

Each of the cooling units 142a through 142i of the cooling panel 130 comprises a plurality of Peltier devices 156.

Specifically, each of the cooling units 142a through 142i comprises an endothermic substrate 146 held closely against the rear surface of the sensor substrate 38, a plurality of endothermic electrodes 148 disposed at given spaced intervals on the endothermic substrate 146, P-type semiconductor devices 152 and N-type semiconductor devices 154 joined respectively to opposite ends of the endothermic electrodes 148, a plurality of exothermic electrodes 150 each interconnecting the P-type semiconductor device 152 connected to one of the endothermic electrodes 148 and the N-type semiconductor device 154 connected to an adjacent one of the endothermic electrodes 148, and an exothermic substrate 158 held closely against the exothermic electrodes 150.

In FIG. 5, the endothermic substrate 146, the endothermic electrodes 148, the P-type semiconductor devices 152 and the N-type semiconductor devices 154, the exothermic electrodes 150, and the exothermic substrate 158 are stacked successively in this order downwardly from the rear surface of the sensor substrate 38, thereby making up each of the cooling units 142a through 142i.

Each of the Peltier devices 156 is made up of two adjacent endothermic electrodes 148, an exothermic electrode 150 extending between the two endothermic electrodes 148, and a P-type semiconductor device 152 and an N-type semiconductor device 154 that are interconnected by the exothermic electrode 150. The temperature controller 133 comprises a DC power supply 144 connected to the endothermic electrode 148 that is joined to the leftmost P-type semiconductor device 152 in FIG. 5, and the endothermic electrode 148 that is joined to the rightmost N-type semiconductor device 154 in FIG. 5.

The endothermic substrate 146 and the exothermic substrate 158 are preferably made of a thermally conductive material, e.g., ceramics exhibiting a thermal conductivity that is oriented from the sensor substrate 38 toward the cooling units 142a through 142i.

As described above, the photoelectric conversion layer 51 (see FIG. 3) of the sensor substrate 38 is made of amorphous selenium. Since amorphous selenium tends to change in structure and lose functions thereof at high temperatures, amorphous selenium needs to be used within a certain temperature range. The radiation solid-state detecting device 26 includes the temperature regulation controller 135 (see FIG. 1) for cooling the sensor substrate 38 when the temperature of the photoelectric conversion layer 51 (amorphous selenium) exceeds the temperature range, thereby keeping the temperature of the photoelectric conversion layer 51 within the given temperature range.

The temperature sensor 138 of the temperature regulation controller 135, which is disposed near the sensor substrate 38, detects the temperature of the sensor substrate 38 depending on the temperature of the amorphous selenium, at all times or at certain time intervals, and outputs the detected temperature of the sensor substrate 38 to the temperature controller 133. The temperature controller 133 determines whether the input temperature of the sensor substrate 38 exceeds a given upper-limit temperature depending on the upper-limit value of the temperature range for the photoelectric conversion layer 51 (amorphous selenium). If the temperature controller 133 judges that the temperature of the sensor substrate 38 has exceeded the upper-limit temperature, then the temperature controller 133 supplies direct current from the DC power supply 144 to the Peltier devices 156, and energizes the fan 140. When the Peltier devices 156 are supplied with direct current, they exhibit a phenomenon referred to as the Peltier effect. Specifically, the junctions between the endothermic electrodes 148 and the P-type semiconductor devices 152 and the N-type semiconductor devices 154 absorb heat from the amorphous selenium in the sensor substrate 38 through the endothermic substrate 146, and the junctions between the P-type semiconductor devices 152 and the N-type semiconductor devices 154 and the exothermic electrodes 150 radiate heat that has been transferred from the junctions of the endothermic electrodes 148 through the P-type semiconductor devices 152 and the N-type semiconductor devices 154, through the exothermic substrate 158, and out of the cooling panel 130. The fan 140 applies air to the exothermic substrate 158 to cool the exothermic substrate 158 and to promote the radiation of heat therefrom.

The upper-limit temperature referred to above may be pre-registered in the temperature controller 133, or it may be pre-registered as one of the image capturing conditions in the controller 28, and transmitted from the controller 28 via the communication unit 136 to the temperature controller 133 before a radiation image is captured.

Figure 6:
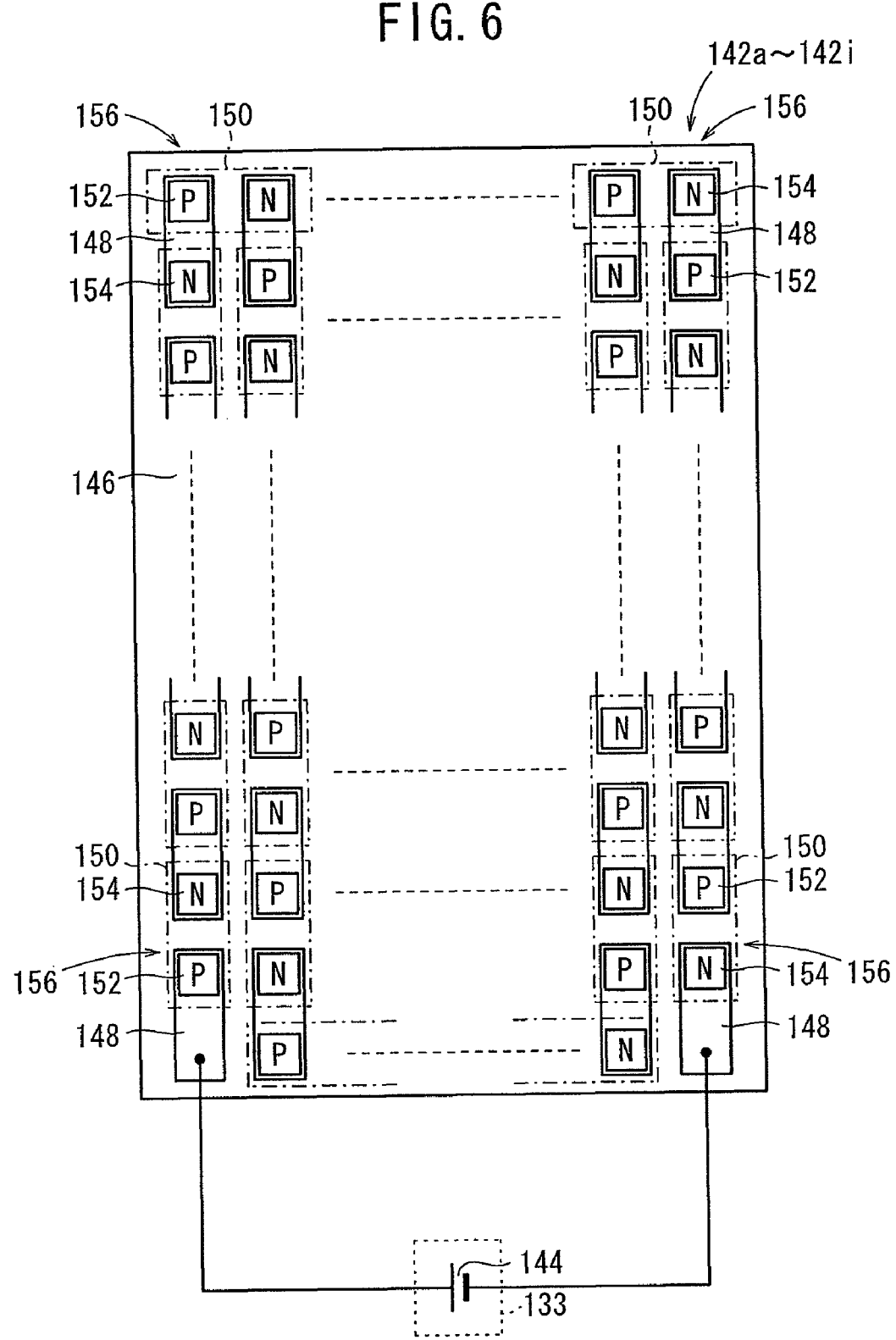
FIG. 6 is a plan view showing the layout of Peltier devices disposed in each of the cooling units shown in FIG. 2.

FIG. 6 shows in plan view the layout of the Peltier devices 156 disposed in each of the cooling units 142*a* through 142*i*. The sensor substrate 38 and the exothermic substrate 158 (see FIGS. 1 through 3, 5) are omitted from illustration. In FIG. 6, the Peltier devices 156 are shown as viewed in a direction from the exothermic substrate 158 toward the sensor substrate 38.

As shown in FIG. 6, in each of the cooling units 142*a* through 142*i*, the Peltier devices 156 are arrayed in a matrix on the endothermic substrate 146. When the Peltier devices 156 are supplied with direct current from the DC power supply 144, each of the Peltier devices 156 absorbs heat from the amorphous selenium of the sensor substrate 38 and radiates heat through the exothermic substrate 158 (see FIG. 5) and out of the cooling panel 130. The temperature controller 133 (see FIG. 1) of the cooling panel energizing unit 132 can selectively supply direct current from the DC power supply 144 to the cooling units 142*a* through 142*i* and radiate the heat of the amorphous selenium in given areas of the sensor substrate 38, which face the cooling units 142*a* through 142*i*, through the cooling units 142*a* through 142*i* and out of the cooling panel 130.

The area specifying unit 134 (see FIG. 1) specifies pixels 50 in which to record radiation image information based on the image capturing conditions transmitted from the controller 28 via the communication unit 136, and outputs data from each of the specified pixels 50 as a recording area for the radiation image information to the timing control circuit 48, the temperature controller 133, the timing control signal detector 270, and the exposure detector 272. Therefore, the controller 28 preferably should send the image capturing conditions to the area specifying unit 134 in order to cause the area specifying unit 134 to specify the recording areas, before the subject 22 is irradiated with radiation X, or more specifically, before the radiation X reaches the irradiated surface of the sensor substrate 38 and stores electric charges in the storage capacitors 53 (see FIG. 3).

Based on the supplied recording areas, the timing control circuit 48 outputs a timing control signal to the gate line driving circuit 44 and the signal reading circuit 46, in order to read image signals from the specified pixels 50. Based on the supplied recording areas, the temperature controller 133 supplies direct current from the DC power supply 144 to the Peltier devices 156 (see FIGS. 5 and 6) of the cooling units 142*a* through 142*i*, which face the specified pixels 50.

The timing control signal detector 270 detects the timing control signal output from the timing control circuit 48, and outputs the detected timing control signal as an image information output detection signal to the temperature controller 133. Specifically, since the radiation image information is read from the pixels 50 (see FIG. 3) as recording areas in response to the timing control signal output from the timing control circuit 48 to the gate line driving circuit 44 and the signal reading circuit 46, the timing control signal detector 270 detects the reading of radiation image information from the pixels 50, and outputs the detected reading as the image information output detection signal to the temperature controller 133 and to the timer 280. Since the area specifying unit 134 outputs the recording areas to the timing control signal detector 270, the timing control signal detector 270 is able to monitor (detect) whether or not the timing control circuit 48 has supplied the timing control signal for only the pixels 50 as the recording areas.

Based on the recording areas supplied from the area specifying unit 134, the exposure detector 272 detects the storage of electric charges in the storage capacitors 53, or the generation of electric charges in the photoelectric conversion layer 51 of those pixels 50 which are not specified as recording areas, and outputs the detected storage or generation as an image recording detection signal to the temperature controller 133 and to the timer 280. Specifically, when electric charges are stored in the storage capacitors 53 or generated in the photoelectric conversion layer 51 by exposure to radiation X, the radiation image information is recorded in the pixels 50. The exposure detector 272 detects the recording of radiation image information in the unspecified pixels 50, i.e., the exposure to radiation X, and outputs the detected recording as the image recording detection signal to the temperature controller 133 and to the timer 280.

When the temperature controller 133 is supplied with the image recording detection signal and/or the image information output detection signal, the temperature controller 133 judges that radiation image information is being recorded or that the recorded radiation image information is being read. The temperature controller 133 then stops supplying direct current from the DC power supply 144 to the Peltier devices 156 and de-energizes the fan 140, thereby temporarily stopping the performing of temperature regulation on the sensor substrate 38.

The timer 280 starts measuring time from the time (stop time) when direct current stops being supplied from the DC power supply 144 to the Peltier devices 156. When the timer 280 has measured a preset period of time from the stop time, the timer 280 outputs a timing signal representing the measured preset time period to the temperature controller 133.

Since the timing control signal detector 270 outputs the image information output detection signal to the timer 280, and the exposure detector 272 outputs the image recording detection signal to the timer 280, the timer 280 measures time from the stop time to a time when the timer 280 stops being supplied with the image information output detection signal or with the image recording detection signal, and outputs the timing signal to the temperature controller 133 at the time when the timer 280 stops being supplied with the image information output detection signal or with the image recording detection signal. Therefore, the preset period of time referred to above represents a period of time from the stop time to the time when the timer 280 stops being supplied with the image information output detection signal or with the image recording detection signal.

Based on the timing signal supplied from the timer 280 to the temperature controller 133, the temperature controller 133 judges that recording or reading of the radiation image information has been completed. The temperature controller 133 supplies direct current from the DC power supply 144 to the Peltier devices 156 and energizes the fan 140, thereby resuming temperature regulation on the sensor substrate 38.

The image capturing system 20 basically is constructed as described above. Operations of the image capturing system 20 will be described below with reference to FIGS. 1 through 6.

Using the console 30, the operator, typically a radiological technician, sets ID information concerning the subject 22, image capturing conditions, etc. The ID information includes information as to the name, age, sex, etc., of the subject 22, which can be acquired from an ID card possessed by the subject 22. The image capturing conditions include, in addition to information concerning the region of the subject 22 to be imaged, an image capturing direction, etc., as specified by the doctor in charge of the subject 22, an irradiation dose of the radiation X depending on the region to be imaged, and the upper-limit temperature for the sensor substrate 38, which corresponds to the upper-limit value of the temperature range for amorphous selenium. If the image capturing system 20 is connected to a network, then these items of information can be acquired from a higher-level apparatus through the network. Alternatively, such items of information can be entered from the console 30 by an operator.

After the region to be imaged of the subject 22 has been positioned with respect to the radiation solid-state detecting device 26, the controller 28 controls the radiation generator 24 and the radiation solid-state detecting device 26 according to set image capturing conditions. Based on the image capturing conditions sent from the controller 28 via the communication unit 136, the area specifying unit 134 of the radiation solid-state detecting device 26 specifies pixels 50 in which to record radiation image information, and outputs each of the specified pixels 50 as a recording area for the radiation image information to the timing control circuit 48, the temperature controller 133, the timing control signal detector 270, and to the exposure detector 272.

The temperature sensor 138 detects the temperature of the sensor substrate 38 depending on the temperature of the amorphous selenium, at all times or at certain time intervals, and outputs the detected temperature of the sensor substrate 38 to the temperature controller 133. Based on the input recording areas, the temperature controller 133 selects corresponding ones from among the cooling units 142*a* through 142*i* to which to supply direct current from the DC power supply 144, and determines whether the temperature of the sensor substrate 38 has exceeded a given upper-limit temperature, depending on the upper-limit value of the temperature range for the photoelectric conversion layer 51 (amorphous selenium), each time that the temperature controller 133 is supplied with the temperature of the sensor substrate 38 from the temperature sensor 138, which may occur at all times or at certain time intervals.

The radiation generator 24 applies radiation X to the subject 22 according to the image capturing conditions sent from the controller 28. Radiation X which has passed through the subject 22 is converted into electric signals by the photoelectric conversion layer 51 of the pixels 50 in the specified recording areas in the sensor substrate 38 of the radiation solid-state detecting device 26. The electric signals are stored as electric charges in the storage capacitors 53 (see FIG. 3). The stored electric charges, which represent radiation image information of the subject 22, are read from the storage capacitors 53 according to timing control signals, which are supplied from the timing control circuit 48 to the gate line driving circuit 44 and the signal reading circuit 46.

As described above, since the area specifying unit 134 outputs the recording areas to the timing control circuit 48, the timing control circuit 48 outputs timing control signals based on the recording areas to the gate line driving circuit 44 and the signal reading circuit 46, in order to read image signals from the pixels 50 of the storage capacitors 53 where electric charges have been stored based on the recording areas.

Specifically, the gate line driving circuit 44 selects one of the gate lines 54 according to the timing control signal from the timing control circuit 48, and supplies a drive signal to bases of the TFTs 52 that are connected to the selected gate line 54. The multiplexer 60 of the signal reading circuit 46 successively switches between the signal lines 56 connected to the reading ICs 42 in order to select one of the signal lines 56 at a time. An electric charge representing the radiation image information that is stored in the storage capacitor 53 of the pixel 50, which corresponds to the selected gate line 54 and the selected signal line 56, is supplied through the resistor 64 to the operational amplifier 66. The operational amplifier 66 integrates the supplied electric charges and supplies them through the multiplexer 60 to the A/D converter 62, which converts the electric charges into a digital image signal. The digital image signal is supplied through the communication unit 136 to the image processor 32. After all the image signals have been read from the pixels 50 connected to the selected gate line 54, the gate line driving circuit 44 selects the next gate line 54, and supplies a drive signal to the selected gate line 54. The signal reading circuit 46 then successively reads image signals from the TFTs 52 connected to the selected gate line 54, in the same manner as described above. The above operations are repeated to read two-dimensional radiation image information stored in the pixels 50 as specified recording areas in the sensor substrate 38, and to supply the read two-dimensional radiation image information to the image processor 32.

Radiation image information supplied to the image processor 32 is processed thereby. The display device 34 displays an image based on the processed radiation image information from the image processor 32 for diagnostic purposes. The doctor makes a diagnosis based on the image displayed on the display device 34.

The temperature controller 133 (see FIG. 1) sequentially determines whether (the temperature of the sensor substrate 38 depending on) the temperature of the amorphous selenium in the recording areas has exceeded (the upper-limit temperature of the sensor substrate 38 depending on the upper-limit value of) the temperature range for amorphous selenium. If the temperature controller 133 judges that the temperature of the sensor substrate 38 has exceeded the upper-limit temperature, then the temperature controller 133 selects those from among the cooling units 142*a* through 142*i* which face the recording areas, supplies direct current from the DC power supply 144 to the Peltier devices 156 of the selected cooling units 142*a* through 142*i*, and energizes the fan 140.

The Peltier devices 156 that are supplied with direct current exhibit a phenomenon referred to as the Peltier effect, i.e., the junctions between the endothermic electrodes 148 and the P-type semiconductor devices 152 and the N-type semiconductor devices 154 absorb heat of the amorphous selenium from the sensor substrate 38 through the endothermic substrate 146. The junctions between the P-type semiconductor devices 152 and the N-type semiconductor devices 154 and the exothermic electrodes 150 radiate heat that has been transferred from the junctions of the endothermic electrodes 148 through the P-type semiconductor devices 152 and the N-type semiconductor devices 154, through the exothermic substrate 158 and out of the cooling panel 130. The fan 140 applies air to the exothermic substrate 158 to cool the exothermic substrate 158 and to promote the radiation of heat therefrom.

If the temperature controller 133 judges that the temperature of the sensor substrate 38 detected by the temperature sensor 138 has become lower than the upper-limit temperature, then the temperature controller 133 stops supplying direct current from the DC power supply 144 to the Peltier devices 156 and de-energizes the fan 140.

The area specifying unit 134 also outputs the specified recording areas to the timing control signal detector 270 and to the exposure detector 272. The timing control signal detector 270 monitors (detects) whether the timing control circuit 48 has supplied the timing control signal for only the pixels 50 specified as the recording areas. If the timing control signal detector 270 detects the output of the timing control signal from the timing control circuit 48, the timing control signal detector 270 outputs the detected output as an image information output detection signal to the temperature controller 133 and to the timer 280. When the exposure detector 272 detects the storage of electric charges in the storage capacitors 53, or the generation of electric charges within the photoelectric conversion layer 51 of those pixels 50 which are not specified as the recording areas, based on the recording areas supplied from the area specifying unit 134, the exposure detector 272 outputs the detected storage or generation as an image recording detection signal to the temperature controller 133 and the timer 280.

When the temperature controller 133 is supplied with the image recording detection signal and/or the image information output detection signal, the temperature controller 133 judges that radiation image information has started to be recorded in the pixels 50 specified as the recording areas, or that the recorded radiation image information has started to be read from the pixels 50 specified as recording areas. The temperature controller 133 then stops supplying direct current from the DC power supply 144 to the Peltier devices 156 and de-energizes the fan 140, thereby stopping temperature regulation from being performed on the sensor substrate 38.

The timer 280 starts measuring time, from a time (stop time) when direct current stops being supplied from the DC power supply 144 to the Peltier devices 156. Thereafter, when the timer 280 stops being supplied with the image information output detection signal from the timing control signal detector 270, or with the image recording detection signal from the exposure controller 272, the timer 280 stops measuring time and outputs a timing signal to the temperature controller 133.

In response to the timing signal supplied from the timer 280 to the temperature controller 133, the temperature controller 133 judges that recording or reading of the radiation image information has been completed. The temperature controller 133 supplies direct current from the DC power supply 144 to the Peltier devices 156 and energizes the fan 140, thereby resuming temperature regulation on the sensor substrate 38.

In the image capturing system 20 according to the present embodiment, the radiation solid-state detecting device 26 includes the sensor substrate 38, the temperature regulation controller 135 for performing a temperature regulation control operation to adjust the sensor substrate 38 to a predetermined temperature, the timing control signal detector 270 for detecting the reading (output) of the radiation image information from the sensor substrate 38 and for outputting the detected reading as an image information output detection signal to the temperature regulation controller 135, and the timer 280. When the temperature regulation controller 135 is supplied with the image information output detection signal, the temperature regulation controller 135 stops the temperature regulation control operation from being performed on the sensor substrate 38. When the timer 280 has measured the preset period of time, from a stop time when the temperature regulation control operation on the sensor substrate 38 is stopped, the temperature regulation controller 135 resumes the temperature regulation control operation on the sensor substrate 38 based on the timing signal that is output from the timer 280 to the temperature regulation controller 135.

Therefore, when radiation image information is read (output), the temperature regulation controller 135 temporarily stops the temperature regulation control operation from being carried out on the sensor substrate based on the image information output detection signal. As a result, noise due to the temperature regulation control operation is prevented from being added to the radiation image (radiation image information), and hence a high quality radiation image is produced.

Since the temperature regulation control operation performed on the sensor substrate 38 is resumed after the preset period of time has elapsed from temporary shutoff of the temperature regulation control operation, the temperature regulation control operation is reliably disabled during time periods in which the temperature regulation control operation is not required, and the temperature regulation control operation is performed appropriately only during time periods other than when radiation image information is being read. Accordingly, the radiation solid-state detecting device 26 operates stably at all times. As a result, unnecessary control of temperature regulation is avoided in order to conserve energy that is consumed by the radiation solid-state detecting device 26 and by the overall image capturing system 20.

The exposure detector 272 detects the recording of radiation image information in the sensor substrate 38, i.e., the application of radiation X to the sensor substrate 38, and outputs the detected recording as an image recording detection signal to the temperature regulation controller 135. Based on the supplied image recording detection signal and/or the image information output detection signal, the temperature regulation controller 135 temporarily stops the temperature regulation control from being performed on the sensor substrate 38. The temperature regulation controller 135 thus stops the temperature regulation control operation on the sensor substrate 38 not only when radiation image information is being read (output), but also when radiation image information is recorded. Consequently, noise caused by the temperature regulation control operation is reliably prevented from being added to the radiation image information, and a high quality radiation image is produced.

After the temperature regulation control operation has been temporarily stopped due to the radiation image information starting to be recorded, the temperature regulation controller 135 resumes the temperature regulation control operation, based on a timing signal output from the timer 280 to the temperature regulation controller 135, once the timer 280 has measured the preset period of time from the stop time. Since the temperature regulation control operation is resumed upon elapse of the preset period of time from temporary stoppage of the temperature regulation control operation, the temperature regulation control operation is reliably disabled during time periods in which the temperature regulation control operation is not required, such as during times when the radiation image information is not being recorded. The temperature regulation control operation is performed appropriately only during time periods other than when radiation image information is being recorded or read. Accordingly, the radiation solid-state detecting device 26 operates stably at all times. As a result, unnecessary temperature regulation control is avoided in order to conserve energy consumed by the radiation solid-state detecting device 26 and by the overall image capturing system 20.

The timer 280 measures a time from the stop time until a time when reading (outputting) of radiation image information is completed, i.e., at a time when inputting of the image information output detection signal from the timing control signal detector 270 is stopped, or the timer 280 measures a time from the stop time until a time when recording of the radiation image information is completed, i.e., at a time when inputting of the image recording detection signal from the exposure detector 272 is stopped. After having measured the preset period of time, the timer 280 outputs a timing signal to the temperature regulation controller 135 (temperature controller 133). Accordingly, the temperature regulation controller 135 is capable of resuming the temperature regulation control operation accurately and reliably.

The temperature regulation controller 135 comprises the cooling panel 130, which is disposed on the rear surface of the sensor substrate 38 for cooling the sensor substrate 38, and the cooling panel energizing unit 132 for energizing the cooling panel 130. Therefore, the temperature regulation controller 135 can reliably cool the sensor substrate 38.

The cooling panel 130 comprises the cooling units 142*a* through 142*i* placed on the rear surface of the sensor substrate 38. The temperature controller 133 of the cooling panel energizing unit 132 (the temperature regulation controller 135) energizes those among the cooling units 142*a* through 142*i* that face the specified recording areas. Since the temperature controller 133 selectively energizes the cooling units 142*a* through 142*i* based on the specified recording areas, the specified recording areas are reliably cooled, whereas other areas of the sensor substrate 38 are prevented from being cooled. As a result, the sensor substrate 38 is cooled effectively without wasteful consumption of energy.

The cooling panel energizing unit 132 comprises the temperature controller 133, the temperature sensor 138, and the fan 140. The temperature sensor 138 detects the temperature of the sensor substrate 38 depending on the temperature of the amorphous selenium within the specified recording areas. The temperature controller 133 determines whether or not the detected temperature has exceeded the upper-limit temperature for the sensor substrate 38, depending on the upper-limit value of the temperature range for amorphous selenium. If the temperature controller 133 judges that the detected temperature has exceeded the upper-limit temperature, then the temperature controller 133 energizes the cooling panel 130 and the fan 140 so that (the temperature of the amorphous selenium indicated by) the temperature of the sensor substrate 38 will drop to (the upper-limit value of the temperature range indicated by) the upper-limit temperature. The fan 140 applies air to the cooling panel 130 for promoting radiation of heat, which is transferred from the sensor substrate 38 to the cooling panel 130, and out of the cooling panel 130. Therefore, the cooling panel 130 and the sensor substrate 38 are cooled efficiently.

Each of the cooling units 142*a* through 142*i* comprises the Peltier devices 156, which are arrayed in a matrix on the endothermic substrate 146 and held closely against the rear surface of the sensor substrate 38. The temperature controller 133 cools the specified recording areas by supplying direct current from the DC power supply 144 to the Peltier devices 156. Heat in the sensor substrate 38 is thus reliably radiated out of the cooling panel 130 based on the Peltier effect exhibited by the Peltier devices 156.

Before radiation image information is recorded in the sensor substrate 38, the area specifying unit 134 specifies certain pixels 50 within the sensor substrate 38 as pixels 50 for recording radiation image information, based on the image capturing conditions from the controller 28, and outputs the specified pixels 50 as recording areas to the timing control circuit 48, the temperature controller 133, the timing control signal detector 270, and to the exposure detector 272.

Based on the recording areas, the timing control circuit 48 outputs timing control signals to the gate line driving circuit 44 and to the signal reading circuit 46, for thereby reliably reading image signals from the pixels 50 in which radiation image information has been recorded. Based on the recording areas, the temperature controller 133 supplies direct current from the DC power supply 144 to the Peltier devices 156 of those ones from among the cooling units 142*a* through 142*i* that correspond to the recording areas. Based on the recording areas, the timing control signal detector 270 efficiently detects output of the timing control signal. Based on the recording areas, the exposure detector 272 reliably and efficiently detects the storage of electric charges in the storage capacitors 53, or the generation of electric charges (application of radiation X) in the photoelectric conversion layer 51 of those pixels 50 that are not specified as recording areas.

In the above description, the preset period of time measured by the timer 280 is a period of time from the stop time, referred to above, to the time when the timer 280 stops being supplied with either the image information output detection signal or the image recording detection signal. However, the preset period of time may be set to different periods of time. For example, the timer 280 may supply the timing signal to the temperature controller 133 after elapse of a predetermined period of time from the time the timer 280 stops being supplied with either the image information output detection signal or the image recording detection signal.

Alternatively, if the period of time (reading time) required to read radiation image information from the sensor substrate 38 and the period of time (recording time) required to record radiation image information in the sensor substrate 38 are known in advance, then the reading time and the recording time may be pre-registered in the timer 280. The timer 280 may then supply the timing signal to the temperature controller 133 when the timer 280 measures the reading time or the recording time from the stop time. In this case, the timer 280 does not need to be supplied with the image information output detection signal or with the image recording detection signal.

In the above description, the cooling panel 130 is disposed on the rear surface of the sensor substrate 38. However, the cooling panel 130 may also be disposed on the irradiated surface of the sensor substrate 38. Even if the cooling panel 130 is disposed on the irradiated surface of the sensor substrate 38, since the cooling panel 130 is disposed on a surface of the sensor substrate 38, the cooling panel 130 offers the same advantages described above according to the present invention.

If the cooling panel 130 is disposed on the irradiated surface of the sensor substrate 38, then the cooling panel 130 should be made of a material that is permeable to radiation X. Since the endothermic electrodes 148, the P-type semiconductor devices 152, the N-type semiconductor devices 154, and the exothermic electrodes 150 of each of the cooling units 142a through 142i contain metals therein, a portion of the radiation X applied to the sensor substrate 38 may potentially be absorbed by such metals. To avoid such a drawback, the layout pattern of the Peltier devices 156 within the cooling units 142a through 142i may be pre-registered, such that when radiation image information is input thereto, a reduction in quality of the radiation image information may be compensated for by an image processing process based on the registered layout pattern. In this manner, the radiation image information is prevented from being adversely affected due to undue absorption of radiation X by the metals.

In the above description, the temperature regulation controller 135 resumes the temperature regulation control operation based on the timing signal from the timer 280. After the temperature regulation controller 135 has resumed the temperature regulation control operation, the temperature controller 133 of the temperature regulation controller 135 performs the following processing operations:

The timer 280 starts measuring a time period, from the time when the timer 280 outputs the timing signal, i.e., from the time (resumption time) when the temperature regulation control operation is resumed. When the timer 280 has measured a preset period of time from the resumption time, the timer 280 outputs a new timing signal to the temperature controller 133, and the temperature controller 133 once again stops the resumed temperature regulation control operation, based on the new timing signal input thereto. Therefore, the overall temperature regulation controller 135 conserves electrical energy, and avoids unnecessary temperature regulation control.

The timer 280 starts measuring a time period, from the time when the timer 280 outputs the timing signal, i.e., from the time (resumption time) when the temperature regulation control operation is resumed. When the timer 280 has measured a preset period of time from the resumption time, the timer 280 outputs a new timing signal to the temperature controller 133. Based on the new timing signal input to the temperature controller 133, the temperature controller 133 outputs a ready signal (recordable signal) via the communication unit 136 to the controller 28, which indicates that a radiation image can be recorded in the sensor substrate 38. Specifically, when the temperature regulation control operation is performed for a certain period of time from the resumption time, the temperature of the amorphous selenium in the sensor substrate 38 becomes stable within a given temperature range. Based on the new timing signal input to the temperature controller 133, the temperature controller 133 sends a ready signal to the controller 28, which can recognize that the temperature of the amorphous selenium has been stabilized as a result of the temperature regulation control operation, thereby making it possible to record a radiation image in the sensor substrate 38. Based on the ready signal input to the controller 28, the controller 28 can control the radiation generator 24 in order to start applying radiation X to the subject 22.

In the present embodiment, instead of the above structure, the temperature regulation control unit 135 may relax the temperature regulation control operation on the sensor substrate 38 based on the image recording detection signal and/or the image information output detection signal, and then after the timer 280 has measured a preset period of time the temperature regulation control unit 135 may stop relaxing to resume the normal temperature regulation control operation. The timer 280 may restart measuring time when the temperature regulation control operation is resumed. Then, when the timer 280 has measured another preset period of time after the temperature regulation control unit 135 has stopped relaxing the temperature regulation control operation, a new time measurement signal is output to the temperature controller 133 of the temperature regulation control unit 135. The temperature controller 133 may relax the temperature regulation control operation again based on the new time measurement signal input, or may output a ready signal to the controller 28 via a communication unit 136.

The temperature regulation control operation may be relaxed by reducing the rotation number of the fan 140 of the temperature regulation control means 135 to half, preferably to ⅓, of the rotation number in the normal operation. The temperature regulation control operation may also be relaxed by reducing the amount of the direct current supplied to the Peltier devices 156 to half, preferably to ⅓, of the amount of the direct current supplied thereto in the normal operation.

By controlling the rotation number of the fan 140 and/or the amount of current supplied to the Peltier devices 156 without stopping the temperature regulation control operation temporally, the same advantages as the aforementioned embodiment can be achieved.

Alternatively, when the temperature regulation control is operated by using both the fan 140 and the Peltier devices 156, the temperature regulation control unit 135 may relax the temperature regulation control operation on the sensor substrate 38 based on the image recording detection signal and/or the image information output detection signal by stopping either the operation of the fan 140 or the operation of the Peltier devices 156.

Figure 7:
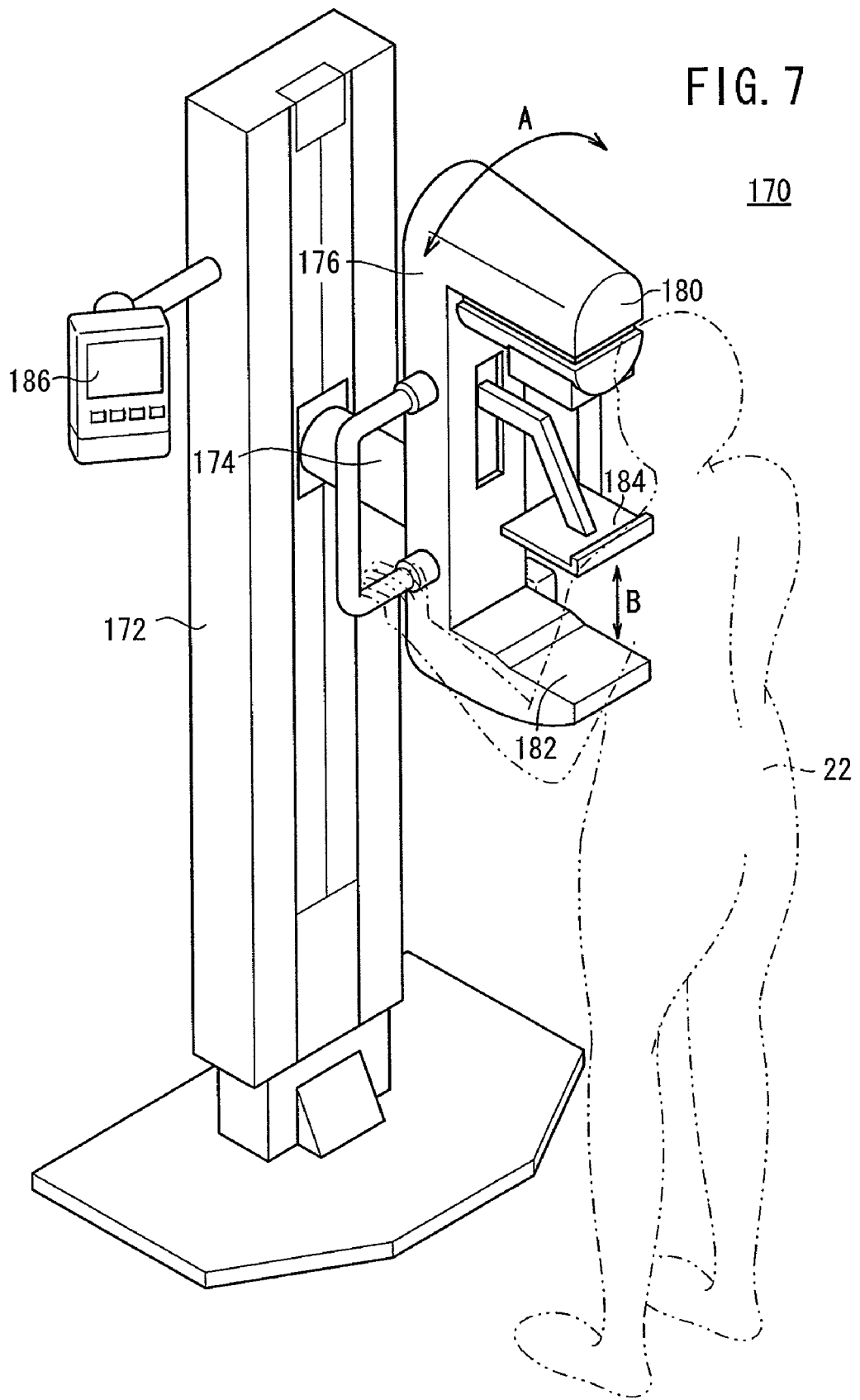
FIG. 7 is a perspective view of a mammographic apparatus which incorporates the image capturing system shown in FIG. 1.

FIG. 7 shows in perspective a mammographic apparatus 170 utilized for breast cancer screening, which incorporates the image capturing system 20 according to the present embodiment.

As shown in FIG. 7, the mammographic apparatus 170 includes an upstanding base 172, a vertical arm 176 fixed to a horizontal swing shaft 174 disposed substantially centrally on the base 172, a radiation source housing unit 180 housing therein a radiation source (not shown) for applying radiation X to a breast 179 (see FIG. 8) of a subject 22 to be imaged and which is fixed to an upper end of the arm 176, an image capturing base 182 mounted on a lower end of the arm 176 in confronting relation to the radiation source housing unit 180, and a compression plate 184 for compressing and holding the breast 179 against the image capturing base 182.

When the arm 176, to which the radiation source housing unit 180 and the image capturing base 182 are secured, is angularly moved about the swing shaft 174 in the directions indicated by the arrow A, an image capturing direction with respect to the breast 179 of the subject 22 can be adjusted. The compression plate 184 coupled to the arm 176 is disposed between the radiation source housing unit 180 and the image capturing base 182. The compression plate 184 is vertically displaceable along the arm 176 in the directions indicated by the arrow B.

A display control panel 186 is connected to the base 172 for displaying image capturing information including an image capturing region, an image capturing direction, etc., of the subject 22, which have been detected by the mammographic apparatus 170, the ID information of the subject 22, etc., and for enabling setting of these items of information, if necessary. The display control panel 186 includes functions that are part of the functions of the console 30 and the display device 34 (see FIG. 1).

Figure 8:
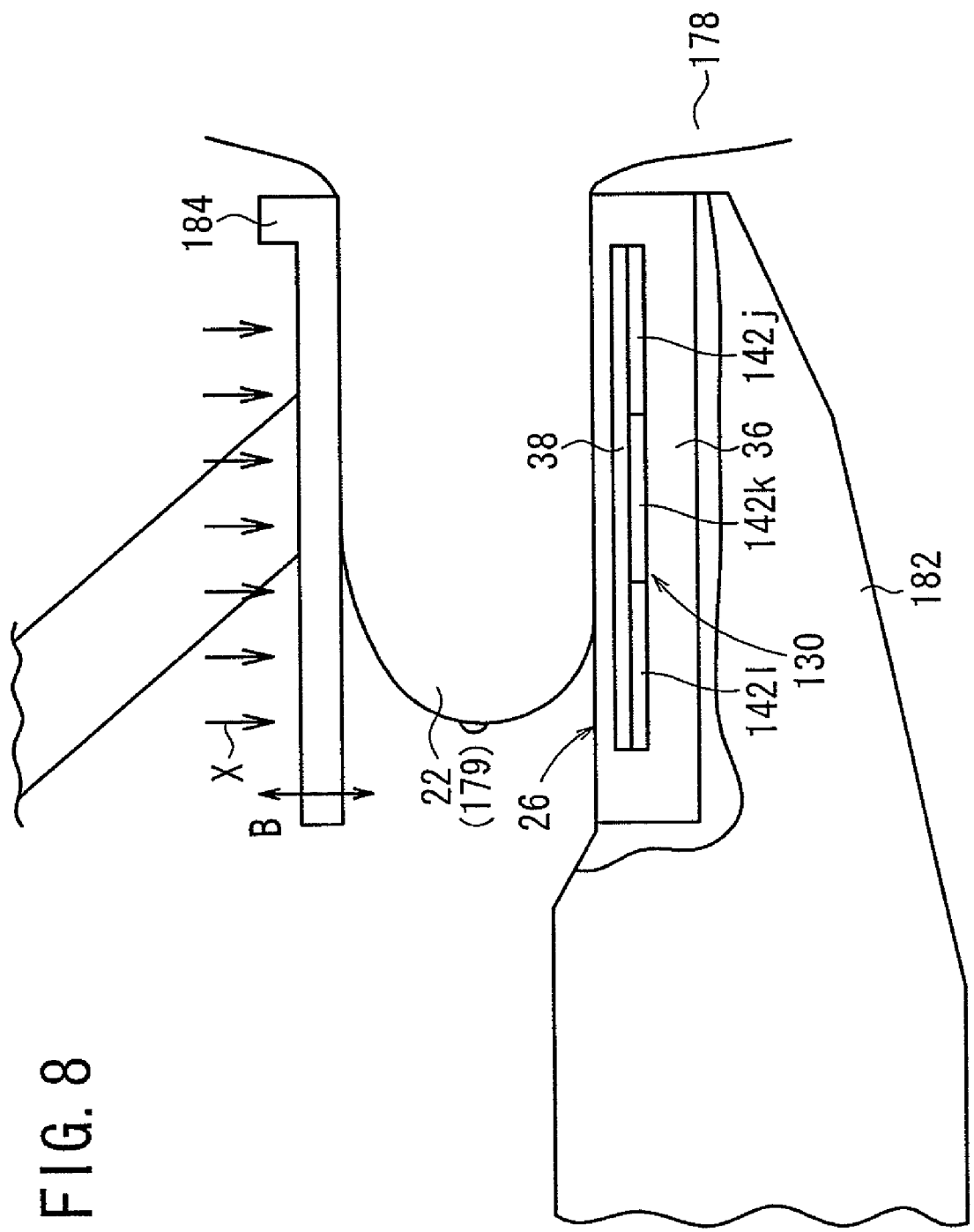
FIG. 8 is a fragmentary vertical elevational view, partly in cross section, showing internal structural details of an image capturing base of the mammographic apparatus shown in FIG. 7.

FIG. 8 shows the internal structural details of the image capturing base 182 of the mammographic apparatus 170. In FIG. 8, the breast 179 of the subject 22 to be imaged is shown as being placed between the image capturing base 182 and the compression plate 184.

The image capturing base 182 houses therein the radiation solid-state detecting device 26 for storing radiation image information, which is captured based on radiation X output from the radiation source in the radiation source housing unit 180, and outputting an electric signal representative of the stored radiation image information. In FIG. 8, the cooling panel 130, which is made up of cooling units 142j through 142l, is disposed on the rear surface of the sensor substrate 38.

In the mammographic apparatus 170 shown in FIGS. 7 and 8, the cooling panel 130 is disposed on the rear surface of the sensor substrate 38. However, the cooling panel 130 may also be disposed on the irradiated surface of the sensor substrate 38.

The radiation solid-state detecting device 26 including the cooling panel 130 disposed on the surface of the sensor substrate 38 is housed in the image capturing base 182. The mammographic apparatus 170 offers the same advantages described above according to the present invention. That is, when the breast 179 touches the radiation solid-state detecting device 26, the body temperature of the subject 22 is transmitted to the sensor substrate 38 through the breast 179 so that the temperature of the sensor substrate 38 rises. Therefore, the region of the sensor substrate 38 corresponding to the region where the breast 179 touches is cooled.

Figure 9:
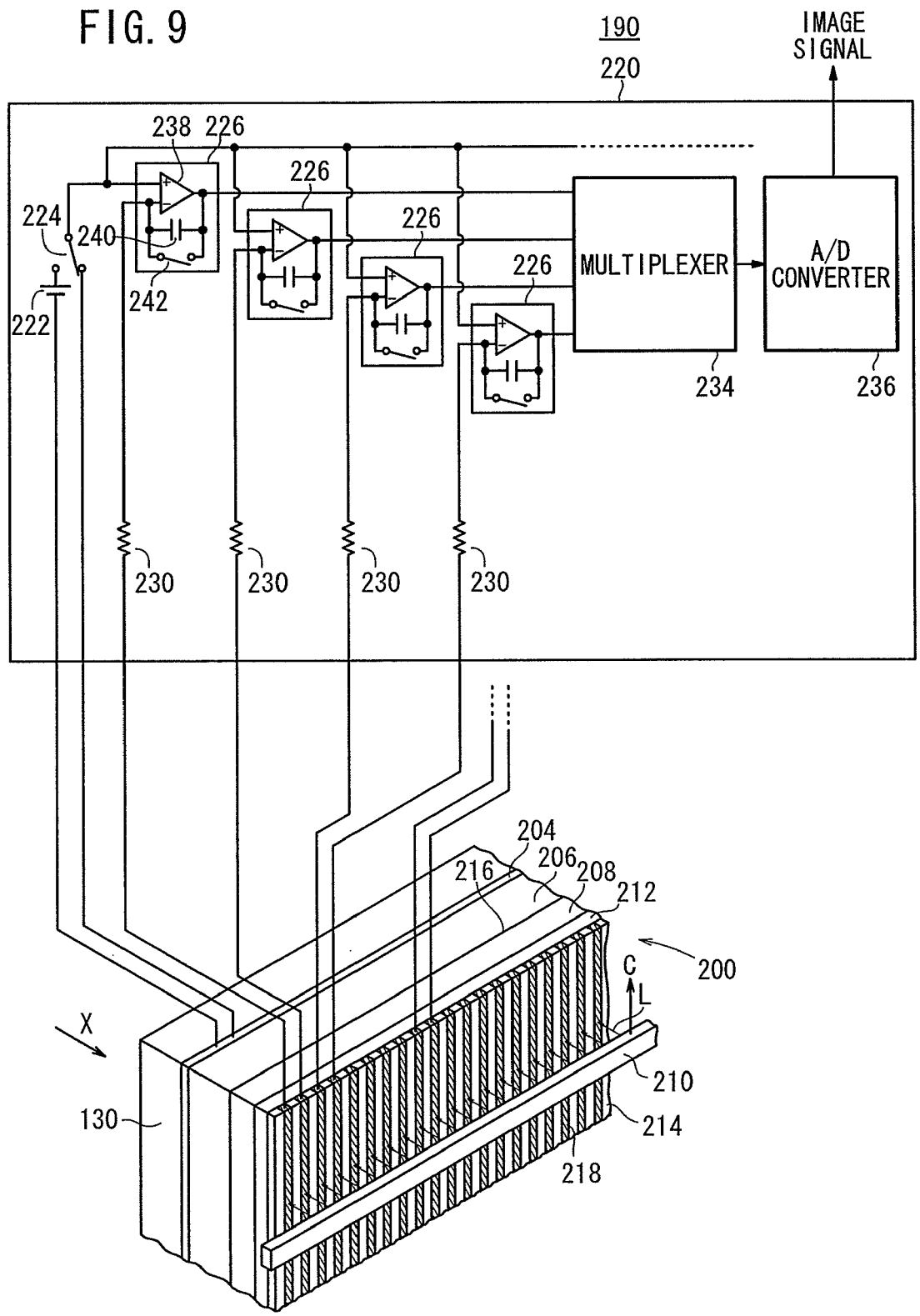
FIG. 9 is a view showing a radiation solid-state detecting device according to another embodiment of the present invention.

FIG. 9 shows a light readout type radiation solid-state detecting device 190 according to another embodiment of the present invention. Unlike the direct conversion type radiation solid-state detecting device 26 shown in FIG. 3 employing TFTs 52, the light readout type radiation solid-state detecting device 190 has a sensor substrate 200 for storing radiation image information as an electrostatic latent image, and which enables reading of the electrostatic latent image as electric charge information when the sensor substrate 200 is irradiated with reading light L from a reading light source 210.

The sensor substrate 200 comprises a first electrode layer 204 permeable to radiation X, a recording photoconductive layer 206 that becomes electrically conductive when irradiated with radiation X, a charge transport layer 208, which acts substantially as an electric insulator with respect to latent image electric charges and as an electric conductor with respect to transport electric charges that have a polarity opposite to the latent image electric charges, a reading photoconductive layer 212 that becomes electrically conductive when irradiated with reading light L from the reading light source 210, and a second electrode layer 214 permeable to the reading light L. The layers are successively arranged in this order, from the surface of the sensor substrate 200 that is irradiated with the radiation X.

A charge storage region 216 for storing the electric charges generated by the recording photoconductive layer 206 is disposed between the recording photoconductive layer 206 and the charge transport layer 208. The second electrode layer 214 comprises a number of linear electrodes 218 extending in the direction indicated by the arrow C, which is perpendicular to the direction in which the reading light source 210 extends. The first electrode layer 204 and the linear electrodes 218 of the second electrode layer 214 are connected to a signal reading circuit 220 for reading electric charge information from the latent image electric charges stored in the charge storage region 216.

The signal reading circuit 220 comprises a power supply 222 and a switch 224 for applying a given voltage between the first electrode layer 204 and the second electrode layer 214 of the sensor substrate 200, a plurality of current detecting amplifiers 226 connected to the linear electrodes 218 of the second electrode layer 214 for detecting currents representing the radiation image information as latent image electric charges, a plurality of resistors 230 connected to the current detecting amplifiers 226, a multiplexer 234 for successively switching between output signals from the current detecting amplifiers 226, and an A/D converter 236 for converting analog image signals from the multiplexer 234 into digital image signals. Each of the current detecting amplifiers 226 comprises an operational amplifier 238, an integrating capacitor 240, and a switch 242.

In FIG. 9, the cooling panel 130 is disposed on the irradiated surface of the sensor substrate 200. However, the cooling panel 130 may also be disposed on the rear surface of the sensor substrate 200.

The radiation solid-state detecting device 190 shown in FIG. 9 operates as follows: The switch 224 is operated to connect the movable contact thereof to the power supply 222, to apply a voltage between the first electrode layer 204 and the second electrode layer 214, whereupon radiation X is applied to the subject 22 (see FIG. 1). Radiation X that has passed through the subject 22 is applied through the first electrode layer 204 to the recording photoconductive layer 206. The recording photoconductive layer 206 becomes electrically conductive and generates electric charge pairs. Among the generated electric charge pairs, positive electric charges are combined with negative electric charges supplied from the power supply 222 to the first electrode layer 204, and the positive electric charges disappear. The negative electric charges generated by the recording photoconductive layer 206 move toward the charge transport layer 208. Since the charge transport layer 208 acts substantially as an electric insulator with respect to the negative electric charges, the negative electric charges are stored as an electrostatic latent image in the charge storage region 216, which is present as an interface between the recording photoconductive layer 206 and the charge transport layer 208.

After the electrostatic latent image has been stored in the sensor substrate 200, the signal reading circuit 220 reads the radiation image information. The switch 224 is operated to connect the movable contact thereof between the non-inverting input terminals of the operational amplifiers 238 of the current detecting amplifiers 226 and the first electrode layer 204 of the sensor substrate 200.

While the reading light source 210 moves in the auxiliary scanning direction indicated by the arrow C, the reading light source 210 applies reading light L to the reading photoconductive layer 212. The switches 242 of the current detecting amplifiers 226 are turned on and off in the auxiliary scanning direction at intervals corresponding to the pixel pitch, for thereby reading the radiation image information as electric charge information representing the electrostatic latent image.

When reading light L is applied through the second electrode layer 214 to the reading photoconductive layer 212, the reading photoconductive layer 212 becomes electrically conductive and generates electric charge pairs. Among the generated electric charge pairs, positive electric charges reach the charge storage region 216 through the charge transport layer 208, which acts substantially as an electric insulator with respect to the positive electric charges. In the charge storage region 216, the positive electric charges are combined with negative electric charges, which represent the electrostatic latent image stored in the charge storage region 216, and the positive electric charges disappear. The negative electric charges generated by the reading photoconductive layer 212 are recombined with the positive electric charges of the linear electrodes 218 of the second electrode layer 214, and the negative electric charges disappear. When the electric charges disappear, currents are generated by the linear electrodes 218 and read by the signal reading circuit 220 as electric charge information, which represents the radiation image information.

The currents generated by the linear electrodes 218 are integrated by the current detecting amplifiers 226 and supplied as voltage signals to the multiplexer 234. The multiplexer 234 successively switches between the current detecting amplifiers 226 in the main scanning direction along which the linear electrodes 218 are arrayed, and supplies voltage signals to the A/D converter 236. The A/D converter 236 converts the supplied voltage signals, which form an analog image signal, into a digital image signal, and supplies the digital image signal representing the radiation image information to the image processor 32. Each time that radiation image information is read from an array of pixels across the auxiliary scanning direction, the switches 242 of the current detecting amplifiers 226 are turned on to discharge the electric charges stored in the integrating capacitors 240. The above operations are repeated while the reading light source 210 moves in the auxiliary scanning direction, as indicated by the arrow C, in order to read the two-dimensional radiation image information stored in the sensor substrate 200.

In the image capturing system 20, which incorporates the radiation solid-state detecting device 190 therein, the cooling panel 130 is disposed on the surface of the sensor substrate 38. Therefore, the image capturing system 20 that incorporates the radiation solid-state detecting device 190 offers the same advantages described above according to the present invention.

Rather than the direct conversion type radiation solid-state detecting device 26 or the light readout type radiation solid-state detecting device 190 for converting applied radiation X directly into electric charge information, an indirect conversion type radiation detector including a scintillator for converting applied radiation X into visible light may be employed, together with a detecting device for converting the visible light into electric charge information.

Instead of the TFTs 52, such a device as a CCD (Charge Coupled Device), a CMOS (Complementary Metal Oxide Semiconductor) device or the like may be used for a direct or indirect conversion type radiation detecting device.

Although certain preferred embodiments of the present invention have been shown and described in detail, it should be understood that various changes and modifications may be made to the embodiments without departing from the scope of invention as set forth in the appended claims.

What is claimed is:

1. An image detecting device comprising:
    an image detector for recording an image therein and outputting the recorded image as image information;
    a temperature regulation controller for performing a temperature regulation control operation in order to adjust the image detector to a predetermined temperature;
    an image information output detector for detecting the output of the image information from the image detector, and outputting the detected output as an image information output detection signal to the temperature regulation controller; and
    a timer,
    wherein the temperature regulation controller stops a temperature regulation control operation on the image detector based on the image information output detection signal input thereto, and resumes the temperature regulation control operation on the image detector when the timer has measured a preset period of time after the temperature regulation control operation has been stopped.

2. An image detecting device according to claim 1, further comprising:
    an image recording detector for detecting the recording of the image in the image detector, and outputting the detected recording as an image recording detection signal to the temperature regulation controller,
    wherein the temperature regulation controller stops the temperature regulation control operation on the image detector based on the image recording detection signal or the image information output detection signal input thereto, and resumes the temperature regulation control operation on the image detector when the timer has measured a preset period of time after the temperature regulation control operation has been stopped.

3. An image detecting device according to claim 2, wherein the timer measures a preset period of time from a time when the temperature regulation controller stops the temperature regulation control operation to a time when the output of the image information has been completed, or from the time when the temperature regulation controller stops the temperature regulation control operation to a time when recording of the image has been completed.

4. An image detecting device according to claim 2, further comprising:
    an area specifying unit for specifying a pixel for recording the image in the image detector, and outputting the specified pixel as a recording area for the image information to the temperature regulation controller, the image information output detector, and the image recording detector;
    wherein the image information output detector detects the image information output from the pixel as the recording area;
    the image recording detector detects the image recorded in a pixel that is not specified as the recording area in the image detector; and
    the temperature regulation controller performs the temperature regulation control operation on the pixel of the recording area.

5. An image detecting device according to claim 1, wherein the temperature regulation controller again stops the resumed temperature regulation control operation, when the timer has measured a preset period of time from a time when the temperature regulation controller has resumed the temperature regulation control operation.

6. An image detecting device according to claim 1, wherein the temperature regulation controller outputs a recordable signal indicating that the image can be recorded in the image recorder to an outside, when the timer has measured a preset period of time from the time when the temperature regulation controller has resumed the temperature regulation control operation.

7. An image detecting device according to claim 1, wherein the temperature regulation controller comprises:
   a cooling panel disposed on a surface of the image detector for cooling the image detector; and
   a cooling panel energizing unit for energizing the cooling panel.

8. An image detecting device according to claim 7, wherein the cooling panel comprises:
   a plurality of cooling units disposed on the surface of the image detector,
   wherein the cooling panel energizing unit energizes those from among the cooling units that correspond to recording areas of the image detector in which the image is recorded.

9. An image detecting device according to claim 7, wherein the cooling panel energizing unit comprises:
   a temperature sensor for detecting a temperature of the image detector;
   a temperature controller for energizing the cooling panel to cool the image detector in order to lower the temperature thereof to a predetermined temperature; and
   a cooling fan for applying air to the cooling panel to cool the cooling panel.

10. An image detecting device according to claim 7, wherein the cooling panel comprises a matrix of Peltier devices disposed on the surface of the image detector,
   wherein the cooling panel energizing unit supplies current to the Peltier devices to cool the image detector.

11. An image detecting device according to claim 1, wherein the image detecting device comprises a radiation image information detecting device, wherein the image detector records radiation having passed through a subject and applied to a surface of the image detector as a radiation image, and outputs the recorded radiation image as radiation image information;
   the cooling panel is disposed on either the surface of the image detector that is irradiated with the radiation, or on an opposite rear surface of the image detector; and
   the cooling panel is permeable to the radiation if the cooling panel is disposed on the surface of the image detector that is irradiated with the radiation.

12. An image detecting device according to claim 11, wherein the image detecting device comprises a radiation solid-state detecting device for storing the radiation having passed through the subject as electric charge information, and reading the stored electric charge information as the radiation image information.

13. An image detecting device according to claim 12, wherein the radiation solid-state detecting device comprises a light readout type detector for reading the stored electric charge information as the radiation image information in response to reading light being applied thereto.

14. An image capturing system comprising:
   an image detecting device according to claim 1; and
   a controller for controlling the image detecting device.

15. An image capturing system according to claim 14, further comprising:
   a radiation generator for generating and applying radiation to a subject;
   wherein the image detecting device records radiation having passed through the subject as a radiation image, and outputs the recorded radiation image to an outside as radiation image information; and
   the controller controls the radiation generator and the image detecting device.

16. An image detecting device comprising:
   an image detector for recording an image therein and outputting the recorded image as image information;
   a temperature regulation controller for performing a temperature regulation control operation in order to adjust the image detector to a predetermined temperature;
   an image information output detector for detecting the output of the image information from the image detector, and outputting the detected output as an image information output detection signal to the temperature regulation controller; and
   a timer,
   wherein the temperature regulation controller relaxes a temperature regulation control operation on the image detector based on the image information output detection signal input thereto, and stops relaxing the temperature regulation control operation on the image detector when the timer has measured a preset period of time after the temperature regulation control operation has been relaxed.

17. An image detecting device according to claim 16, further comprising:
   an image recording detector for detecting the recording of the image in the image detector, and outputting the detected recording as an image recording detection signal to the temperature regulation controller,
   wherein the temperature regulation controller relaxes the temperature regulation control operation on the image detector based on the image recording detection signal or the image information output detection signal input thereto, and stops relaxing the temperature regulation control operation on the image detector when the timer has measured a preset period of time after the temperature regulation control operation has been relaxed.

18. An image detecting device according to claim 17, wherein the timer measures a preset period of time from a time when the temperature regulation controller relaxes the temperature regulation control operation to a time when the output of the image information has been completed, or from the time when the temperature regulation controller relaxes the temperature regulation control operation to a time when recording of the image has been completed.

19. An image detecting device according to claim 17, further comprising:
   an area specifying unit for specifying a pixel for recording the image in the image detector, and outputting the specified pixel as a recording area for the image information to the temperature regulation controller, the image information output detector, and the image recording detector;
   wherein the image information output detector detects the image information output from the pixel as the recording area;
   the image recording detector detects the image recorded in a pixel that is not specified as the recording area in the image detector; and
   the temperature regulation controller performs the temperature regulation control operation on the pixel of the recording area.

20. An image detecting device according to claim 16, wherein the temperature regulation controller again relaxes the resumed temperature regulation control operation, when the timer has measured a preset period of time from a time when the temperature regulation controller has stopped relaxing the temperature regulation control operation.

21. An image detecting device according to claim 16, wherein the temperature regulation controller outputs a recordable signal indicating that the image can be recorded in the image recorder to an outside, when the timer has measured a preset period of time from the time when the temperature regulation controller has stopped relaxing the temperature regulation control operation.

* * * * *